United States Patent [19]

Huber

[11] Patent Number: 5,470,991
[45] Date of Patent: Nov. 28, 1995

[54] PROCESS FOR THE MANUFACTURE OF FURAN DERIVATIVES

[75] Inventor: Ulrich Huber, Zurich, Switzerland

[73] Assignee: Givaudan-Roure Corporation, Clifton, N.J.

[21] Appl. No.: 70,418

[22] PCT Filed: Oct. 2, 1992

[86] PCT No.: PCT/CH92/00199

§ 371 Date: Jun. 3, 1993

§ 102(e) Date: Jun. 3, 1993

[87] PCT Pub. No.: WO93/07134

PCT Pub. Date: Apr. 15, 1993

[30] Foreign Application Priority Data

Oct. 11, 1991 [CH] Switzerland ............... 2994/91

[51] Int. Cl.$^6$ ............... C07D 307/02
[52] U.S. Cl. ............... 549/479
[58] Field of Search ............... 549/479

[56] References Cited

U.S. PATENT DOCUMENTS

| | | | |
|---|---|---|---|
| 3,910,966 | 10/1975 | Evers et al. | 549/479 |
| 3,917,869 | 11/1975 | Evers et al. | 549/479 |
| 3,922,288 | 11/1975 | Evers et al. | 549/479 |
| 3,989,856 | 11/1976 | Evers et al. | 549/479 |
| 3,996,250 | 12/1976 | Evers et al. | 549/479 |
| 4,020,170 | 4/1977 | von den Ouweland et al. | 549/479 |
| 4,020,175 | 4/1977 | Evers | 549/472 |
| 4,055,578 | 10/1977 | Evers | 549/479 |
| 4,988,526 | 1/1991 | Brüning et al. | 549/479 |
| 5,145,703 | 8/1992 | Emberger et al. | 549/479 |

FOREIGN PATENT DOCUMENTS 1543653  4/1979  United Kingdom.

OTHER PUBLICATIONS

Fronowitz et al II CA 58: 2041 f (1963).
Fronowitz et al I CA 87: 53022 m (1977).
A. F. Thomas et al., Tett. Lett., 27, No. 4, (1986) 505–6.
V., Jaeger et al., "Methoden Der Organischen Chemic (Houben–Weyl)", vol. V/20, (1977), 743–751.
D. Obrecht, Helvetica Chimica Acta, 72 (1989) 447–456.
S. Gronowitz et al., J. Het Chem., 14 (1977) 281–288.
R. G. Jones et al., J. Am. Chem. Soc., 75 (1953) 4048–4052.

*Primary Examiner*—C. Warren Ivy
*Assistant Examiner*—A. A. Owens
*Attorney, Agent, or Firm*—George M. Gould; George W. Johnston; Mark E. Waddell

[57] ABSTRACT

The invention is concerned with a process for the manufacture of substituted furans which are, in particular, flavorants; thereby 4-hydroxy-2-yn-1-ones or acetals or ketals thereof are cyclized with nucleophilic S-compounds to 3-S-furans, whereby this 3-S atom can be optionally substituted, and the acetylene derivatives, the 4-hydroxy-2-yn-1-ones, can be optionally 1- and/or 4-alkyl or alkenyl substituted.

7 Claims, No Drawings

PROCESS FOR THE MANUFACTURE OF FURAN DERIVATIVES

This application is a 371 of PCT/CH92/00199 filed Oct. 2, 1992.

The invention is concerned with a process for the manufacture of substituted furans; thereby 4-hydroxy-2-yn-1-ones or acetals or ketals thereof are cyclized with nucleophilic S-compounds to 3-S-furans, whereby this 3-S atom can be optionally substituted, and the acetylene derivatives, the 4-hydroxy-2-yn-1-ones, can be optionally 1- and/or 4-alkyl or alkenyl substituted.

More particularly, the invention is concerned with a process for the manufacture of substituted furan derivatives of the formula

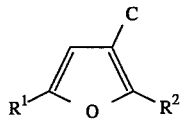
I wherein $R^1$ and $R^2$ signify hydrogen, $C_{1-6}$-alkyl, such as $CH_3$, $C_2H_5$ or $C_{2-6}$-alkenyl, such as propenyl, etc. and C represents a sulphur-containing radical —B or —S—R, defined below.

The process comprises cyclizing an acetylene derivative

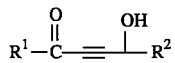
II or an acetal or ketal thereof using a reagent III which contains at least one nucleophilic sulphur atom

AB    III wherein
$A=H^+$, $NH_4^+$, $N(C_{1-6}\text{-alkyl})_3H^+$, an alkali metal cation, an alkaline earth metal cation, substituted by halogen (F, Cl, Br, I), OH, SH, C=O or a $C_{1-6}$-carboxylic acid residue or a $C_{1-6}$-alkylcarboxylic acid derivative, e.g. —$CH_2(CH_2)_2COOC_2H_5$, —$CH_2CH(CH_3)CH_2COCH_3$, —$CH_2CH(CH_3)SH$, $C_{1-6}$-acyl, e.g. $C_{1-6}$-alkanoyl, such as acetyl, butyryl, substituted (optionally also heterocyclically) $C_{1-6}$-acyl, e.g. 2-tetrahydrofuranylmethylcarbonyl, $R^5=C_{1-6}$-alkyl, e.g. $CH_3$, aryl, e.g. phenyl, heteroaryl, especially residues of 5-ring compounds, such as furyl or thiophenyl, and optionally converting the primary reaction product of the formula

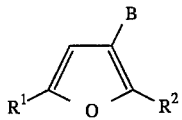
I' by a secondary reaction into a subsequent product of the formula

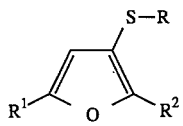
I'' wherein $R=R^4$; or $SR^5$, e.g. S—$C_{1-6}$-alkyl, such as S—$CH_3$, S-sec.butyl, etc., S—$C_{1-6}$-alkyl functionalized with halogen, hydroxy, SH, carbonyl, carboxyl, S-alkyl, such as thiophenyl, S-heteroaryl, such as thio-furfuryl; 3-S-thio-furyl; 3-S-thiophenyl, whereby all (hetero)aryls in the scope of the present invention can be optionally substituted by $R^1$ and $R^2$ and all hydrocarbon residues can be straight-chain or branched.

The process can be represented schematically as follows:

Scheme

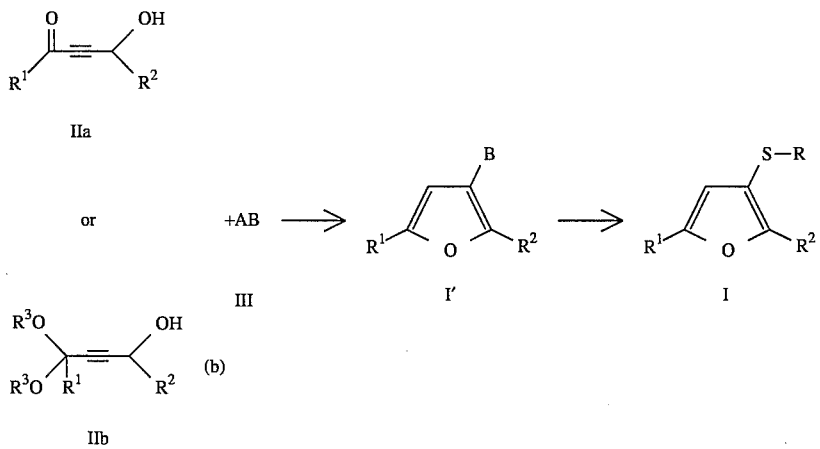

$B=R^4$—$S^-$, $SCN^-$, $AS_2O_3^-$, $H_2NC(=S)NH^-$, $R^5$—$S(=O)O^-$, $R^5$—$S$—$S^-$, and $R^4$=H, $C_{1-6}$-alkyl, e.g. methyl, sec.butyl,
$C_{2-6}$-alkenyl, e.g. propenyl, 2-methyl-butenyl, etc.,
$C_{2-6}$-alkynyl, e.g. butynyl (1), propynyl (1), $C_{1-6}$-alkyl The starting materials II and III are conveniently brought together in the ratio of about 2:1 to about 1:5, preferably about 1:1, with the addition of a mineral acid, such as nitric acid, phosphoric acid or, preferably, sulphuric acid, or an organic acid, e.g. acetic acid, citric acid, etc., and an organic solvent, such as an aliphatic or aromatic, optionally halogenated hydrocarbon, an ether, an alcohol, etc., such as pentane, methylene chloride, toluene, diethyl ether, tetrahydrofuran, MTBE, ethanol, etc., and stirred at temperatures of about 0° to about 100° C., preferably about 20°–50° C.

Preferably, II is added dropwise to III and processed at pH values below about 4. In certain cases it has been observed that prior base treatment of the mixture of starting materials II+III expedites the addition of B in the β-position of II. As bases there can preferably be used in this case tertiary amines, such as e.g. $N(C_2H_5)_3$, diazabicyclooctane, p-diaminopyridine, etc. The suitable temperatures are about 20° to about 50° C. This procedure is indicated especially when $AB=R^4SH$, $R^5-S-S-H$, etc.

The reaction of II with III can be carried out in a one-phase or two-phase (polar/apolar) system. The latter variant is preferred. In the case of the first variant, the reaction is preferably carried out in polar solvents, such as alcohols, e.g. ethanol, etc., acetone, acetonitrile, water, etc. or mixtures of such solvents.

The acetalization or ketalization of II is effected in a manner known per se and the meanings of $R^3$ in formula II(b) are:

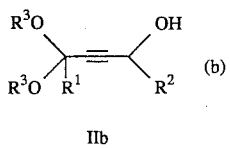

IIb $R^3=C_{1-4}$-alkyl $R^3+R^3+C$ of IIb=5- or 6-membered ring.

The radical B of compound I' can be subjected to subsequent reactions, whereby the compound I" results. The nature of the subsequent reaction depends especially on the nature of B.

For the secondary reactions I'→I" the following generally applies: reactions α) to δ) hereinafter are standard reactions which are well-known to a person skilled in the art and the given parameters, such as reagents, reaction conditions etc., are therefore to be understood to be purely illustrative.

α) Hydrolysis or alcoholysis

—SCN

—SC(=O)—CH₃ or to —SH or to —S—S— ("dimers" of I')

—S—C(=NH)—NH₂ a) carried out using $H^+/H_2O$ in polar solvents (e.g. EtOH, H₂O, etc.) or b) carried out using $HO^-/R^5O^-$ ($R^5$=Me, Et, t-butyl, etc.)

in polar solvents (EtOH, H₂O, etc.)

T=0°–100° C., e.g. about 20° C.

β) Reduction

—SCN

—SC(=O)—CH₃ or —S-acyl (e.g. butyryl)

—S—C(=NH)—NH₂ to —SH

—S—SO₃A

—S—S—R⁵

—S(O)₂—R⁵ to —S—R⁵

Reducing agent e.g. NaBH₄, LiAlH₄, NaBH₃CN

Sn/HCl, Zn/CH₃COOH, Na₂SO₃ phosphine (e.g. tributylphosphine)

as well as Na/NH₃ or

H₂ cat. (cat.=e.g. Pd, Pt, Rh, etc.)

preferably in polar solvents such as H₂O/EtOH, acetic acid, ether, MTBE, tetrahydrofuran, etc.

T=about –80° C. to about 100° C., e.g. 20° C.

γ) Oxidation

—SH to —S—S— ("dimers" of I')

using I2 or H₂O₂ in polar solvents (e.g. EtOH, H₂O)

T=0°–100° C.

δ) Substitution

Namely at the S-atom in the 3-position of compound I' by exchange of the side-chain residue bonded to this S, e.g. by the new side-chain residue R⁴ or SR⁵ using suitable reagents; it can be effected e.g. in accordance with —SCN to —SR⁴ (1), —SCOCH₃ to —SS—$C_{1-6}$-alkyl (2), —SC(=NH)NH₂ to —SS-heteroaryl (3), e.g. dimers of I'

—S—SO₃H

—SH to —SR⁴ (4)

using the following reagents (1) Hal—R⁴, e.g. CH₃I, Cl(CH)₂COCH₃, BrCH₂COOH, etc., (2) A—S-alkyl, e.g. A—SCH₃, (3) A—S-heteroaryl, e.g. 3-mercaptothiophene, furfurylmercaptan, 3-mercaptofuran, etc., (4) HalR⁴.

From this compilation it will be evident that radical C of formula I embraces the radicals defined by B and S—R.

Conditions:

Preferably in polar solvents, such as H₂O, ethanol, ethers, acids such as acetic acid, optionally using bases, such as the usual hydroxides, carbonates, bicarbonates, alkylates, acetates, tert.amines, etc., at temperatures of about 0° to about 10° C.

Working-up

The working-up is preferably effected by extraction: extraction between water or possibly dilute acid and an organic solvent, such as ether, MTBE, CH₂Cl₂, hexane, pentane, toluene, etc., separation of the organic phases and concentration (evaporation) of the organic solvent.

Purification

This is preferably carried out by distillation or in a given instance by chromatography.

The compounds I are for the most part known and to some extent flavorants which are present in nature, e.g. meat flavours.

Examples of such substances are the mercaptans and disulphides exemplified in the following Examples.

The following can be mentioned as further examples:

Subst. alkyl derivatives

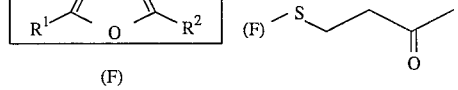

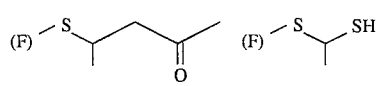

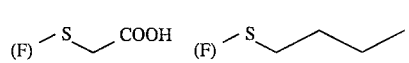

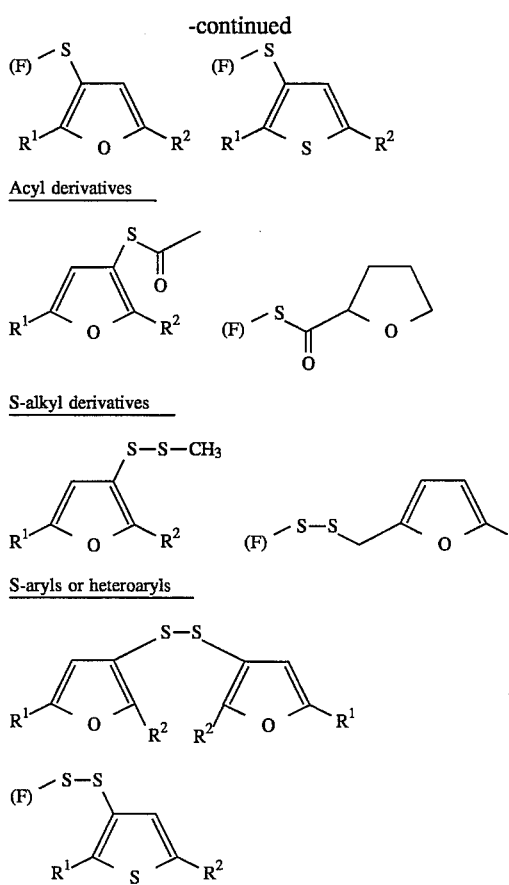

Acyl derivatives

S-alkyl derivatives

S-aryls or heteroaryls

The above mono-S-compounds are accessible by the primary reaction in accordance with the invention.

The above disulphides are accessible especially by one of the subsequent reactions α) to γ), whereby in this case the substitution stands in the foreground.

Formula I, however, also embraces in accordance with the definition compounds I'", namely the compounds

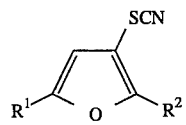

wherein $R^1$ and $R^2$ each independently signify H, $CH_3$ or $C_2H_5$ except that $R^1$ and $R^2$ cannot both be H.

These compounds are novel intermediates for the manufacture of flavorants.

In the case of the flavorants I the compounds which are identical with those found in nature are especially preferred.

EXAMPLE 1

3,3'-Bis-(2,5-dimethylfuryl)-disulphide a) 2,5-Dimethyl-3-thioacetylfuran 5.61 g of 5-hydroxyhex-3-yn-2-one [prepared according to A. F. Thomas et al., Tet. Let. 27, 505, (1986)] in 50 ml of methylene chloride are added dropwise while stirring within 15 min. to a mixture of 11.42 g of thioacetic acid in 50 ml of methylene chloride and 100 ml of 2N sulphuric acid. After leaving to stand at room temperature for 2 hours the mixture is heated to 40° C. and stirred at 40° C. for a further 4 hrs. The reaction mixture is poured into 100 ml of $H_2O$ and extracted 2× with 100 ml of methylene chloride. The organic phases, dried over $MgSO_4$, are concentrated and fractionally distilled in a high vacuum (65° C./0.2 mbar). There are obtained 5.7 g (67% of theory) of a yellow liquid.

NMR ($CDCl_3$) 2.22 ppm (s/3H); 2.26 (s/3H); 2.38 (s/3H); 5.89 (s/1H).

b) 3,3'-Bis-(2,5-dimethylfuryl)-disulphide 2 g of the thioacetate obtained above are dissolved in 25 ml of methanol and treated with 250 mg of sodium carbonate. After stirring at 50° C. for 3 hours the reaction mixture is partitioned between water and ether and the organic phase is dried over magnesium sulphate and concentrated. The 1.3 g of crude-product obtained are distilled at 100° C./0.13 mbar.

NMR ($CDCl_3$) 2.09 ppm (s/6H); 2.24 (s/6H); 5.97 (s/2H).

EXAMPLE 2

3,3'-Bis-(2-methylfuryl)-disulphide a) 2-Methyl-3-thioacetylfuran

The procedure described in Example 1 a is followed, but 4-hydroxy-2-pentynal diethyl acetal [prepared according to R. G. Jones and M. J. Mann, J. Am. Chem. Soc. 75, 4048, (1953)] is used in place of 5-hydroxyhex-3-yn-2-one. There is obtained in 12% yield a yellow liquid (b.p. 35° C./0.2 mbar).

NMR ($CDCl_3$): 2.3 ppm (s/3H); 2.4 (s/3H); 6.35 (d/1H); 7.4 (d/1H).

b) 3,3'-Bis-(2-methylfuryl)-disulphide

The thioacetate obtained above is reacted in accordance with Example 1b. There is obtained the desired product, b.p. 77° C./0.4 mbar.

NMR ($CDCl_3$) 2.1 ppm (s/6H); 6.38 (s/2H); 7.28 (s/2H).

EXAMPLE 3

3-3'-Bis-(2,5-dimethylfuryl)-disulphide a) 3-(2,5-Dimethylfuryl)-thiocyanate 1300 ml of pentane are added to a solution of 115.3 g of sodium rhodanide in 1300 ml of 2N sulphuric acid. Then, 145 g of 5-hydroxyhex-3-yn-2-one [prepared according to A. F. Thomas et al., Tet. Let. 27, 505, (1986)] are added dropwise thereto within 120 minutes while stirring. The phases are separated and the aqueous phase is extracted 2× with 1000 ml of pentane. The combined organic phases are washed with 250 ml of saturated NaCl solution, dried over $MgSO_4$, concentrated and fractionally distilled in a high vacuum (53° C./0.14 mbar). There are obtained 94.8 g (48% of theory) of a yellow liquid.

NMR ($CDCl_3$): 2.22 ppm (s/3H); 2.38 (s/3H); 6.06 (s/1H).

b) 3-3'-Bis-(2,5-dimethylfuryl)-disulphide 7.6 g of sodium hydroxide are dissolved in 200 ml of $H_2O$ and 14.6 g of the thiocyanate obtained above are added dropwise within 30 minutes while stirring. After 90 minutes at room temperature the reaction mixture is partitioned between water and pentane, the organic phase is dried over $MgSO_4$, concentrated and distilled in a high vacuum at 100° C./0.13 mbar. There are obtained 9.2 g (76% yield) of a yellow liquid.

NMR spectrum see Example 1b.

EXAMPLE 4

3-Methylthio-2,5-dimethylfuran 3-(2,5-Dimethylfuryl)-thiocyanate (prepared according to Example 3a) in 50 ml of methanol is added dropwise while stirring within 40 minutes to a solution of 13.7 g of sodium hydroxide and 35.6 g of methyl iodide in methanol. Then, the reaction mixture is poured into 500 ml of $H_2O$ and extracted 3× with 700 ml of methyl tert-butyl ether. The organic phases, dried over $MgSO_4$, are concentrated and distilled in a water-jet vacuum at 71° C./19 mbar. There are thus obtained 22.8 g (70% of theory) of a clear oil.
NMR($CDCl_3$); 2.22 ppm (s/3H); 2.25 (s/3H); 2.28 (s/3H); 5.94 (s/1H).

EXAMPLE 5

2,5-Dimethyl-3-furanthiol (an especially preferred compound)

126.8 g of potassium carbonate and 12.7 g of sodium dithionite are dissolved in 400 ml of water, then 200 ml of 2-mercaptoethanol and 8.5 g of 3-(2,5-dimethylfuryl)-thiocyanate (prepared according to Example 3a) are added dropwise in succession while stirring. After standing at room temperature for 30 min. the reaction mixture is brought to pH 2 slowly with 200 ml of conc. hydrochloric acid and the aqueous phase is extracted 3× with 300 ml of pentane. The organic phases, dried over $MgSO_4$, are concentrated and distilled on a water-jet vacuum at 80° C./13 mbar. There are obtained 4.5 g (57% yield) of a red liquid.
NMR ($CDCl_3$): 2,22 ppm (s/3H); 2,27 (s/3H); 2,62 (d/1H); 5,88 (s/1H).

EXAMPLE 6

2-Methyl-3-furanthiol (an especially preferred compound)

a) 3-(2-Methylfuryl)-thiocyanate

The procedure described in Example 3a is followed, but 4-hydroxy-2-pentynal diethyl acetal [prepared according to R. G. Jones and M. J. Mann, J. Am. Chem. Soc. 75, 4048 (1953)] is used in place of S-hydroxyhex-3-yn-2-one. After fractional distillation in a high vacuum at 51° C./0.6 mbar 3-(2-methylfuryl)thiocyanate is obtained in 80% yield.
NMR ($CDCl_3$): 2.42 ppm (s/3H); 6.5 (d/1H); 7.37 (d/1H).
b) 2-Methyl -3-furanthiol 0.6 g of sodium borohydride is added to a solution of 2.1 g of 3-(2-methylfuryl)-thiocyanate in 20 ml of methanol and the mixture is heated to reflux temperature. After stirring under reflux for 3 hours a further 0.6 g of sodium borohydride is added and the mixture is stirred for a further 15 minutes. Then, the reaction mixture is poured into 50 ml of water and extracted 3× with 50 ml of methyl tert-butyl ether. The combined organic phases are dried over $MgSO_4$ and concentrated. The 1.6 g of crude product obtained are distilled at 140° C./normal pressure.
NMR ($CDCl_3$) 2.33 ppm (s/3H); 2.66 (d/1H); 6.3 (d/1H); 7.25 (d/1H).

EXAMPLE 7

Methyl 2-methyl-3-furyl-disulphide 3-(2-Methylfuryl)thiocyanate (prepared according to Example 6a) is added dropwise while stirring within 25 minutes to a solution of 4.3 g of sodium methylmercaptide in 100 ml of water. After stirring at room temperature for 30 minutes 100 ml of pentane are added and the aqueous phase is separated from the organic phase. The aqueous phase is extracted 2× with 100 ml of pentane. The combined organic phases are dried over $MgSO_4$, concentrated and fractionally distilled in a high vacuum (37° C. 0.48 mbar). The desired product is obtained. NMR ($CDCl_3$); 2.4 ppm (s/3H); 2.45 (s/3H); 6.44 (d/1H); 7.28 (d/1H).

EXAMPLE 8

3-n-Butylthio-2,5-dimethylfuran 6.2 ml of triethylamine and 4.02 g of n-butylmercaptan are simultaneously added dropwise while stirring to a solution of 5 g of S-hydroxyhex-3-yn-2-one [prepared according to A. F. Thomas et al., Tet. Let. 27, 505, (1986)] in 40 ml of methyl tert-butyl ether (MTBE). After 60 minutes at room temperature 70 ml of 5N sulphuric acid are added and the mixture is stirred for a further 60 minutes. Then, the phases are separated, the aqueous phase is extracted with 2×50 ml of MTBE and the organic phase is washed in succession with water, saturated $NaHCO_3$ solution and saturated NaCl solution. The organic phases, dried over $MgSO_4$, are concentrated and fractionally distilled in a high vacuum (63° C./0.25 mbar). There are obtained 6.34 g (77% yield) of the desired product.
NMR ($CDCl_3$): 0.88 ppm (t/3H); 1.46 (multiplet/4H); 2.22 (s/3H); 2.28 (s/3H); 2.58 (t/2H); 5.6 (s/1H).

EXAMPLE 9

3-Methylthio-2,5-dimethylfuran

The procedure described in Example 8 is followed, but methylmercaptan is used in place of n-butylmercaptan. After fractional distillation in a water-jet vacuum (58° C./22 mbar) there is obtained a clear oil in 65% yield. Spectra: see Example 4.

EXAMPLE 10

3-Methylthio-2,5-dimethylfuran

The same product as described in Example 9 is also obtained when 5-hydroxyhex-3-yn-2-one is added dropwise to a mixture of sodium methanethiolate in water and methyl tert-butyl ether and thereupon, as in Example 8, the mixture is treated with sulphuric acid and worked-up.

EXAMPLE 11

3-3'-Bis-(2,5-dimethylfuryl)-disulphide 5 g of S-hydroxyhex-3-yn-2-one in 25 ml of ether are added dropwise while stirring to a mixture of 6.6 g of sodium hydrogen sulphide monohydrate in 20 ml of buffer pH 9 (borax/boric acid) and 30 ml of ether. After stirring for 3 hours the mixture is acidified and stirred for one hour. The organic phase is separated, concentrated and chromatographed in hexane over silica gel. The concentrated top fractions give pure product which is identical with the product from Example 1a.

I claim:
1. A process for the manufacture of compounds of the formula

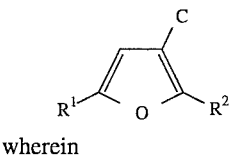

I wherein $R^1$ and $R^2$ signify hydrogen, $C_{1-6}$-alkyl or $C_{2-6}$-alkenyl and C represents a sulphur-containing radical, which process comprises, as a primary reaction, cyclizing a compound

   II or an acetal or ketal thereof using a reagent III which contains at least one nucleophilic sulphur atom

AB   III wherein $A = H^+$, $NH_4^+$, $N(C_{1-6}\text{-alkyl})_3H^+$, an alkali metal cation, or an alkaline earth metal cation, and $B = R^4—S^-$, $SCN^-$, $AS_2O_3^-$, $H_2N—C(=S)NH—$, $R_5—S(=O)O^-$, or $R_5—S—S^-$, wherein $R^4 = H$, $C_{1-6}$-alkyl, $C_{2-6}$-alkenyl, $C_{2-6}$-alkynyl, $C_{1-6}$-alkyl substituted by halogen, OH, SH, C=O, a $C_{1-6}$-carboxylic acid residue, a $C_{1-6}$-alkylcarboxylic acid derivative, $C_{1-6}$-acyl or optionally substituted acyl, and $R^5 = C_{1-6}$-alkyl, aryl, or heteroaryl, and, if desired, converting the primary reaction product of the formula

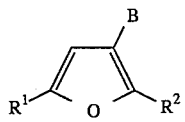   I' into a subsequent product of the formula

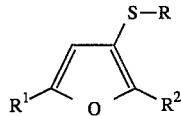   I'' wherein $R = R^4$; or $SR^5$ in which $SR^5$ represents (i) $S—C_{1-6}$-alkyl optionally functionalized with halogen, hydroxy, SH, carbonyl or carboxyl, (ii) S-aryl or (iii) S-heteroaryl.

2. A process according to claim 1, wherein the cyclization is carried out under acidic conditions, whereby this acidic cyclization is optionally preceeded by a basic pre-treatment of the mixture of reactants II and III.

3. A process according to claim 1 or 2, wherein the primary reaction product of formula I' is converted into the subsequent product of the formula I'' in a secondary reaction, wherein the secondary reaction is a hydrolysis, a reduction, an oxidation or a substitution.

4. A process according to claim 1 or 2, wherein the acetal or ketal of compound II is a compound of formula

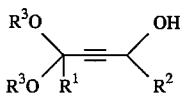   IIb and wherein:

$R^1$, $R^2$ are H or $C_{1-3}$-alkyl, $R^3$ is $CH_3$ or $C_2H_5$, $R^4$ is H, $C_{1-6}$-alkyl or $C_{1-6}$-acyl, $R^5$ is $CH_3$ or phenyl, R is H, $CH_3$, $—S—CH_3$, or optionally substituted S-heteroaryl, including 3-S-furyl, 3-S-thio-furyl, and thiofurfuryl, and B is $SCN^-$, $AS_2O_3^-$, $CH_3S^-$, or $CH_3COS^-$.

5. A process according to claim 4, wherein R signifies H, $CH_3$ or $CH_3S^-$.

6. A process according to claim 4, wherein R is hydrogen, $R^1$ is hydrogen or methyl and $R^2$ is methyl.

7. Compounds of the formula

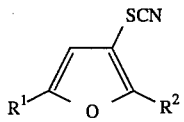   I''' in which $R^1$ and $R^2$ each independently signify H, $CH_3$ or $C_2H_5$, except that $R^1$ and $R^2$ cannot both equal H.

* * * * *

UNITED STATES PATENT AND TRADEMARK OFFICE
CERTIFICATE OF CORRECTION

PATENT NO. : 5,470,991

DATED : November 28, 1995

INVENTOR(S): Ulrich Huber

It is certified that error appears in the above-identified patent and that said Letters Patent is hereby corrected as shown below:

In claim 1, column 9, line 17, change "$H_2N-C(=S)NH-$" to --$H_2N-C(=S)NH^--$--.

In claim 1, column 9, line 18, change "$R_5-S(=O)O^-$" to --$R^5-S(=O)O^-$-- and "$R_5-S-S^-$" to --$R^5-S-S^-$--.

Signed and Sealed this

Sixth Day of May, 1997

Attest:

BRUCE LEHMAN

*Attesting Officer*     *Commissioner of Patents and Trademarks*